US005710183A

United States Patent [19]
Halow

[11] Patent Number: 5,710,183
[45] Date of Patent: Jan. 20, 1998

[54] LAXATIVE/ANTIDIARRHEAL COMPOSITION COMPRISING POLYETHYLENE GLYCOL AND FIBER BULKING AGENT

[76] Inventor: George M. Halow, 4003 Santa Anna, El Paso, Tex. 79902

[21] Appl. No.: 502,773

[22] Filed: Jul. 14, 1995

[51] Int. Cl.$^6$ ........................................ A61K 9/16
[52] U.S. Cl. .................. 514/892; 514/723; 424/78.31; 424/195
[58] Field of Search .................... 514/892, 723; 424/283, 195

[56] References Cited

U.S. PATENT DOCUMENTS

| | | | |
|---|---|---|---|
| 3,202,578 | 8/1965 | Parker | 162/56 |
| 3,211,614 | 10/1965 | Embring et al. | 167/56 |
| 3,725,541 | 4/1973 | Queuille et al. | 424/80 |
| 4,321,263 | 3/1982 | Powell et al. | 424/195 |
| 4,588,589 | 5/1986 | Sheth et al. | 424/195.1 |
| 4,828,842 | 5/1989 | Furst et al. | 424/195.1 |
| 4,978,529 | 12/1990 | Denick, Jr. | 424/480 |
| 4,999,200 | 3/1991 | Casillan | 424/480 |
| 5,077,048 | 12/1991 | Kimura et al. | 424/422 |
| 5,124,144 | 6/1992 | Georgette et al. | 514/892 |
| 5,219,573 | 6/1993 | Tarka, Jr. et al. | 424/439 |
| 5,445,831 | 8/1995 | Leis et al. | 514/892 |

OTHER PUBLICATIONS

Fordtram, Derwent abstract WO, 870212 (1986).

*Primary Examiner*—James H. Reamer
*Attorney, Agent, or Firm*—Hoffman, Wasson & Gitler

[57] ABSTRACT

The invention provides a composition for the improvement of bowel function comprising polyethylene glycol and, preferably, a fiber bulking agent, in, preferably, at least about equal parts by weight of polyethylene glycol; an optional wetting agent to promote solubility/dispersability of the composition in liquid medium; and an optional gas-reducing agent to counteract effects of intestinal gas production attributable to the ingestion of poorly digestible fiber. The products are quickly effective, do not compromise bowel integrity, and are suitable for long-term use in the clinical or veterinary treatment of constipation and/or diarrhea.

33 Claims, No Drawings

LAXATIVE/ANTIDIARRHEAL COMPOSITION COMPRISING POLYETHYLENE GLYCOL AND FIBER BULKING AGENT

BACKGROUND OF THE INVENTION

The invention relates to a composition for the improvement of bowel function. In particular, the invention relates to a rapid-onset composition comprising of polyethylene glycol and a fiber bulking agent which quickly improves bowel motility but does not compromise bowel integrity. The composition further reduces effects of abdominal gas associated with ingestion of poorly digestible fibers. Polyethylene glycol and fiber can be mixed with antiflatulents such as fennel, charcoal, or barley to further reduce gas formation. The invention also relates to methods for improving bowel function by the use of these compositions.

1. Field of the Invention

Laxatives currently commercially available broadly fall into two categories: cathartics which rapidly (within a few hours) improve bowel motility but which adversely affect bowel integrity, as by irritating sensitive bowel membranes; and bulk laxatives, typically based on plant fibers or derivatives thereof, which are much gentler and suitable for long-term use, but which have a markedly slow onset of action and are not tolerated well by a significant number of patients. In particular, bacterial metabolism of indigestible fibers in the colon frequently results in excessive gas production causing bloating, flatulence, and abdominal discomfort or pain. It is accordingly desirable to provide a fiber-based composition for the improvement of bowel motility which combines the gentle action of known fiber-based compositions with rapid efficacy and high patient tolerance, particularly with respect to effects of gas production.

2. Discussion of Related Art

The use of psyllium, cellulose, and other plant fibers for regulation of bowel motility is well-known. As described, for example, in U.S. Pat. No. 4,321,263 to Powell, et al., psyllium-based bulk laxatives have been typically prepared from powdered husks of psyllium seed combined with equal parts of a sugar wetting agent and dispersed in water to provide hydrophilic aqueous compositions which adsorb large amounts of water to provide bulk and thus normalize bowel function by improving stool formation. Owing to the difficulties encountered in the use of such high-sugar preparations, particularly the inability of patients on sugar-restricted diets to use these products, this patent teaches the use instead of a polymer such as polyethylene glycol (PEG), preferably in combination with polyvinylpyrrolidone, as a wetting agent for psyllium powder in amounts of not more than about 10%, preferably from about 2 to 5%, by weight of the wettable granules which are substantially entirely psyllium; the process requires wet granulation of the psyllium powder coated with PEG in a volatile organic solvent such as alcohol, followed by dispersion of these granules in water. The use of PEG as a wetting agent for psyllium or other plant fibers to promote dispersion in an excess of water or alcohol/water medium is also disclosed in U.S. Pat. Nos. 4,978,529 to Denick and 4,828,842 to Furst et al.

Also known is the use of PEG for bowel lavage, as described for example in U.S. Pat. No. 5,077,048 to Kimura, et al. Lavage compositions are commonly used for cleansing the colon before examination or surgery, and are administered just before the procedure. The compositions have for many years typically included large amounts of liquid, electrolytes to preserve serum electrolyte balances, and, more recently, an osmotic agent to reduce water adsorption from the intestine. The Kimura, et al. patent teaches a lavage composition comprising water, PEG as osmotic agent, electrolytes, and organic acid salt. The compositions are orally administered in amounts (generally several liters) sufficient to empty the bowel over a short period of time (usually a few hours), and are not intended for use on a continuing basis.

U.S. Pat. No. 3,211,614 to Embring, et al. describes a laxative composition comprising water, an alkali salt of citric, tartaric, malic or ascorbic acid, and a polyhydroxy alcohol which is mannitol, sorbitol, dulcitol, arabitol, xylitol, or adonitol. Optional ingredients include a small amount of a viscosity-increasing agent. The composition is administered in the form of an enema in an amount sufficient to completely evacuate the colon. U.S. Pat. No. 3,202,578 teaches the use of non-ionic surfactants such as polyoxyalkylene glycols as fecal-softening agents. U.S. Pat. No. 4,999,200 describes psyllium tablet laxative compositions which may employ PEG as binder.

SUMMARY OF THE DISCLOSURE

The invention provides a composition for the improvement of bowel function in mammals, especially humans, comprising a fiber bulking agent, polyethylene glycol, and an optional wetting agent if required for good dispersability of the composition in water. Preferably, the composition further includes a gas-counteracting agent to minimize effects of intestinal gas production attributable to the ingestion of poorly digestible fibers. As compared to known water-based compositions for the improvement of bowel function (laxatives or anti-diarrheals), the compositions of the invention are better-tolerated and faster-acting, with reduced effects from gas production, yet retain the ability of these laxative compositions to gently improve bowel motility without irritating the bowel or otherwise compromising bowel integrity. The products are medically suitable for long-term use in the clinical or veterinary treatment of constipation, and also in the treatment of diarrhea with appropriate fiber selection, such as diarrhea due to abnormal intestinal motililty, e.g. spasm.

DETAILED DESCRIPTION OF THE INVENTION

According to the invention, a composition is provided for the improvement of bowel function, comprising a fiber bulking agent in combination with polyethylene glycol. The fiber of the composition comprises a fiber bulking agent or "dietary fiber" as known in the art which is substantially indigestible and unabsorbable, accordingly passing through the digestive tract without being digested or absorbed, softening stool and increasing stool bulk to thereby stimulate peristalsis and stool elimination. Preferably, the fiber has a high water-retention capacity to further increase stool bulk and/or decrease water content of stools. For treatment of the most common cases of constipation according to the invention, plant-derived fiber bulking agents are generally preferred, such as cellulose or derivatives thereof, particularly cellulose ethers including methylcellulose such as used in Citrucel® [a product of Smith Kline Co.]; psyllium seed husk fiber powder such as used in Metamucil® (a product of Procter and Gamble Co, Cincinnati, Ohio, U.S.A.); or brans such as corn, oat, wheat, or rice brans. Animal-derived fiber or fruit bulking agents may also be used, however, as may synthetic fiber bulking agents. Combinations of different fibers such as water-insoluble and water-soluble fibers are also contemplated. In general, food- or pharmaceutical-grade fiber bulking agents which serve to provide intestinal bulk as known in the art and which are substantially indigestible and unabsorbable, herein also referred to as "dietary fibers", are useful in the composition of the present invention. Bifunctional fibers such as psyllium fiber which are effective for normalizing bowel motility and stool formation in the treatment of both constipation and diarrhea are particularly preferred. Fiber bulking agents described in the art for use in water-based bulk laxatives (or anti-diarrheals) are broadly useful in the present invention. Useful fibers can often be obtained commercially in a form suitable for incorporation into the compositions of the invention, particularly fibers marketed for use in known water-based bulk laxative compositions. Psyllium powder are exemplary.

The fibers may be combined with the PEG as is known for prior art bulk laxative water-based compositions as powder, flake, or in otherwise comminuted particles of suitable size, with the caveat that the fibers should be in a form which provides a palatable drink for liquid administration. To promote uniform dispersion of relatively insoluble fiber particles a water-based drink, a biocompatible wetting agent having good solubility in water may be helpful; for example, the particles may be admixed with a sugar such as dextrose, fructose, or sucrose before or after combining them with a polyethylene glycol. Such wetting agents, as is known, are selected to promote dispersibility/solubility of relatively insoluble particles in a liquid medium and are used in dispersion/solubilisation-effective amounts to provide a relatively smooth liquid composition.

Polyethylene glycol in the amounts used herein unexpectedly contributes to bowel motility improvement in combination with the bulking agent. Any food- or pharmaceutical-grade polymer of polyethylene glycol may be used to prepare the bulk laxative compositions according to the invention for oral administration. Polymers of higher molecular weight (e.g., above about 900) which are solid at room temperature (about 25° C.) and soluble in or miscible with water at room temperature, are currently preferred. Polymers having a molecular weight between about 3000 and 8000 are exemplary; PEG 4000, which is nearly odorless and tasteless and commonly available in USP grade, or PEG 3350 are especially useful. Lower molecular weight polymers such as PEG 400 which are liquid at room temperature are also useful in the practice of the invention, however, but are generally not as effective as higher molecular weight PEGs.

Best Mode of Practice

Compositions according to the invention are easily prepared by simply admixing the fiber bulking agent and PEG. For polyethylene glycols which are solid at room temperature, dry fiber bulking agent is conveniently admixed with comminuted (e.g., powdered) polymer, optionally in the presence of a wetting agent such as described above. The PEG and fiber components are combined in proportions of at least about 50% by weight PEG based on the weight of fiber, and usually at least about 100% by weight PEG based on the amount of fiber, depending upon the fiber characteristics. The ratio of PEG to fiber in the dry composition may range up to about 700% by weight PEG based on the weight of fiber, or more, again depending upon the fiber. Some fiber bulking agents, such as methyl cellulose, are effective according to the invention only in larger amounts, and the dosage volume is kept down by increasing the concentration of fiber in the fiber/PEG composition; conversely, other fiber bulking agents such as psyllium fiber are very effective in smaller amounts, and lower concentrations of such fibers in the fiber/PEG composition can be used. While the ratios of PEG to fiber may be varied considerably within these ranges, in order to maximize the benefits of the invention, it is usually preferable that PEG be present in the dry composition in a weight ratio of solid PEG to dry fiber of at least about 1:2; preferably at least about 1:1; and no more than about 7:1. If the PEG to fiber ratio is too low, rapid onset of activity of the products of the invention drops off and begins to approach the slow onset of the fiber-based bulk laxatives of the prior art. If the PEG to fiber ratio is too high, the volume of composition which must be ingested to obtain the benefits of the fiber component may be inconveniently high, and the excess of PEG may result in undesirable side effects such as those associated with PEG-based bowel lavage compositions. In particular examples, about 3.5 g psyllium powder such as powdered seed husk or about 19 g methyl cellulose describe generically, eg, size of particles, chemical makeup, etc.]are admixed with about 20 g powdered PEG (~3350mw) Spectrum Chemical Mfg. Company, Gardenia, Calif.) to provide a dry fiber/dry PEG composition according to the invention.

For use, the dry fiber/dry PEG composition, with or without wetting agent as needed, is dispersed/dissolved in sufficient water or other aqueous medium to formulate a relatively smooth, palatable drink. Dosages containing from about 15 to 25 g of PEG, typically about 20 g, admixed with fiber or fiber and wetting agent as described above, are conveniently dispersed/dissolved in from about 6 to 10 fl.oz.(about 150 to about 300 g, or about 10–12 times the weight of the solid PEG), conveniently about 8 fl.oz (about 225 g) of water or other palatable water-based liquid such as juice to provide a low-volume drink for oral administration. Two tablespoons of the dry fiber/PEG composition dissolved in 8 oz. of water and administered from 1 to 3 times a day will generally provide satisfactory results. The volume of water or other liquid in which the dry composition is dissolved/dispersed is not critical; in fact, 2 to 3 or more extra glasses of water in conjunction with each drink may be generally beneficial. This dosage can be administered once or more times a day (e.g., tid or qid) on a comparable regimen as known water-based bulking agents until stool formation and/or bowel motility is improved. In common with known bulk laxatives, the product is not habit forming, and can be administered as needed or on a continual basis, usually without significant problem.

Alternate Mode of Practice

In an alternate mode of practice according to the invention, a dry fiber bulking agent of the type described above is combined with liquid PEG (polyethylene glycol polymer which is liquid at room temperature or dissolved powdered PEG). If necessary, a suitable wetting agent is added to the fiber/liquified powder PEG composition to promote dispersal/dissolving of the fiber in the PEG to make a reasonably smooth and palatable drink. Proportions for a suitable liquid PEG/fiber composition comprise, for example, about 2.5 to 25 gms fiber in 8–10 fl oz. of PEG. If desired, the liquid PEG/fiber composition may be further diluted with water for oral administration; for this application, PEG soluble in or miscible with water at room temperature is preferred. Diluted or undiluted, the liquid or liquified powder PEG/fiber composition is conveniently administered orally, in a regimen as described above for diluted dry fiber/solid PEG composition.

In a preferred practice of the invention, the composition (either solid PEG/dry fiber or liquid PEG/dry fiber) further includes a gas-reducing agent such as peppermint, basil, caraway or papaya, which inhibits gas formation to counteract or inhibit gas build-up in the intestine attributable to ingested substantially indigestible fiber. An exemplary, and very effective, gas-reducing agent recommended for inclusion in the compositions of the invention is derived from fennel seed, such as comminuted fennel seed, preferably ground fennel seed, in an amount sufficient to reduce gassy sensations in the patient. Generally, an amount of comminuted fennel seed from about 5% to about 15% by weight of solid PEG is effective for this purpose; about 10% by weight of fennel seed based on the weight of solid PEG in the composition is a recommended starting point. The amount can be increased or decreased according to results as desired, without incurring undesirable side-effects. For a liquid PEG/dry fiber composition, fennel seed is added in comparable amounts.

In yet another embodiment of the invention, the dry or liquid PEG/fiber compositions described above are incorporated into a foodstuff for oral administration. The compositions may be incorporated into food doughs such as bread or cookie doughs, food bars such as nutrition bars or wafers, or combined with other food or flavoring ingredients to make an edible, preferably palatable, product having the above-described properties. The products of the invention can also be formulated in any other ingestible form, with, for example, traditional excipients in a tablet or other medicament as conditions warrant. In whatever the chosen carrier, the proportions of PEG/fiber should be maintained as described above, with smaller or larger dosages (servings) administered per diem as the patient's condition requires. Smaller and more infrequent dosages are recommended for maintenance of comfortable bowel motility, and larger and more frequent dosages are recommended for treatment of acute bowel conditions.

The following Examples are illustrative of making, using, and practicing the invention.

EXAMPLES

I. Polyethylene glycol/psyllium fiber composition.

A. A single dosage dry composition according to the invention was formulated by admixing the following ingredients:

| Ingredient | Amount (in gms) |
| --- | --- |
| Polyethylene glycol 3350* | 20.0 |
| Psyllium fiber** | 3.4 |
| Dextrose*** | 3.1 |
| Ground fennel seed**** | 2.0–3.0 |

*PEG 3350 obtained from Spectrum Chemical Mfg. Co., Gardena, CA, USA]
**Psyllium seed husk fiber obtained from Frontier Chemical Co., Norway, IN, USA
***Dextrose obtained from Spectrum Chemical Co.
****Ground fennel seed obtained from [?]

B. Two teaspoons of the above composition (total 28.5 g) was dispersed/dissolved in 8 fl.oz. water to provide a smooth, palatable drink for oral administration.

II. Polyethylene glycol/methyl cellulose fiber composition.

A. A single dosage dry composition according to IA was formulated, with the exception that 19.0 g of methyl cellulose fiber was substituted for the 3.4 g of psyllium fiber. Two teaspoons of the composition (total 44.10 g) was dispersed/dissolved in 8 fl.oz. of water, as in IB, above.

III. PATIENT: Case Study #1
CASE STUDY:

72-year old gentleman with lower abdominal discomfort, has had extensive surgery; cardiac bypass surgery with pulmonary complications, and had decreased bowel function over a period of time. Patient states it is related to medication. He was on fiber twice/day and given medication of Propulsid (Janssen Corp., Titusville, N.J.) to encourage bowel function, which had helped. Patient was seen in the office on Mar. 11, 1994, and placed on the above formula I, and suspending the previously prescribed Metamucil and Propulsid. Patient responded within three days with significant improvement, much better than on the Metamucil, and no longer needed the Propulsid (a proprietary pro-kinetic drug to help bowl function). Patient was treated for ten days, with the product of formula I, Propulsid and Metamucil were eliminated from the regimen, and bowl function continued normally with the composition. Patient suspended trial after ten days and had to resume his Metamucil twice a day and also resume the Propulsid to keep and improve bowl function. With the special formula and product devised, we were able to eliminate the need for fiber twice a day and the need for Propulsid.

IV. PATIENT: Case Study #3
CASE STUDY:

71-year-old female with previous history of colon surgery. She has history of spastic colon for years, history of colon polyps. Patient has intermittent abdominal discomfort, with history of rectal strictures; she used to dilate herself. She takes laxatives to help move her bowel. Patient has been on twice a day Metamucil, but never really having complete relief, so she takes it periodically. She has to take Ducolax suppositories, but they cause severe pain, and she has incomplete emptying. She has mucus with blood around her stools at times. Patient underwent a colonoscopy for more thorough evaluation; it was an extremely difficult colonoscopy, very redundant, with redundancy of the sigmoid colon and hepatic flexure with a small polyp found that was removed; it was benign. Patient was placed on Propulsid, noting some response with the medication. She has to take Milk of Magnesia with the Propulsid to get better emptying; we tried increasing the dose to 10 mg four times a day, with patient showing some improvement. On January the 10th of 1994, she started on formule I, above. She was seen on January 15th, and was able to take herself off the fiber, Milk of Magnesia, and the Propulsid. She states the formula product was a significant improvement after four days of therapy. She came back to our office wishing for another ten day supply. We gave her a ten day supply, and after continued use of the medication, patient states it was the best product she has ever used, and regretted not getting anymore of the product. Clinically, patient off the formula has to take the Propulsid at this time to help encourage bowel function; she is on 20 mg of Propulsid 3 to 4 times/day. She takes it daily to b.i.d. with fiber, with abdominal bloating and gassy sensation with the fiber, relying on the Propulsid to encourage bowel function. Patient has significant bowel function without the gassy sensation using the formulated product, and was able to suspend three other drugs. EXAMPLE V
PATIENT: Case Study #2
CASE STUDY:

70-year old male with change of bowel pattern, diarrhea and incomplete emptying, and bowel urgency with loose stools. Patient denies any bloating. He has some soreness in the lower abdominal area. Patient underwent colonoscopy exam; he had a very redundant colon with slight chronic irritation. Patient was given formula I of Example I, going from two teaspoons to one and a half teaspoons per day, with patient noting only a little bit of difference initially, but over a period of two or three days, a noted improvement. Patient, after a week of therapy, noted even further treatment response. He came back to the office wanting more of the sample; we gave him another ten day supply, taking one teaspoon to two teaspoons a day, and after ten or twelve days of total therapy, he noted improved response. Patient states that it helped him more than the pro-kinetic drug of Propulsid, with using and adding it to his hobby of making bread, putting it in the bread machine. We have given him an extra sample, and he reports the same effect with eating the formula added to his recipe. Patient, after completion of the trial, went back to Propulsid 10 mg, because he lost the effect of the special formula product. He takes Propulsid 10 mg one to three times per day as needed and fiber.

What is claimed is:

1. A composition for the improvement of bowel function comprising polyethylene glycol and a fiber bulking agent, wherein the polyethylene glycol is present in a weight ratio of polyethylene glycol to fiber of at least about 1:2 and no more than about 7:1.

2. The composition of claim 1, wherein the polyethylene glycol is present in a weight ratio of polyethylene glycol to fiber of at least about 1:1.

3. The composition of claim 2, wherein the polyethylene glycol is a solid at about 25° C.

4. The composition of claim 2, wherein the polyethylene glycol is a liquid at about 25° C.

5. The composition of claim 2, wherein the fiber is psyllium fiber.

6. The compositon of claim 2, wherein the fiber is methyl cellulose fiber.

7. The composition of claim 3, dissolved or dispersed in an aqueous medium.

8. The composition of claim 3, incorporated into a foodstuff.

9. The composition of claim 4, dissolved or dispersed in an aqueous medium.

10. The composition of claim 4, incorporated into a foodstuff.

11. The composition of claim 2, further including a gas-reducing agent in an amount sufficient to counteract intestinal gas production.

12. The composition of claim 11, wherein the gas-reducing agent is derived from fennel seed.

13. The composition of claim 2, further including a wetting agent in an amount sufficient to promote dispersion of the composition in the medium.

14. The composition of claim 13, wherein the wetting agent is a sugar.

15. The composition of claim 4, further including a wetting agent in an amount sufficient to promote dispersion of the composition in the medium.

16. The composition of claim 3, wherein the polyethylene glycol is PEG 3350.

17. The composition of claim 7, wherein the fiber is psyllium, wherein the polyethylene glycol is present in a weight ratio of polymer to fiber of from about 5:1 to about 6:1; and wherein the composition further includes a gas-reducing agent in an amount sufficient to counteract intestinal gas production.

18. The composition of claim 17, wherein the gas-reducing agent is derived from fennel seed.

19. The composition of claim 18, further including a wetting agent in an amount sufficient to promote dispersion of the composition in the medium.

20. The composition of claim 19, wherein the wetting agent is a sugar.

21. The composition of claim 20, wherein the wetting agent is dextrose.

22. The composition of claim 7, wherein the fiber is methyl cellulose, wherein the polyethylene glycol is present in a weight ratio of polymer to fiber of from about 1:1 to about 1.5:1; and wherein the composition further includes a gas-reducing agent in an amount sufficient to counteract intestinal gas production.

23. The composition of claim 22, wherein the gas-reducing agent is derived from fennel seed.

24. The composition of claim 23, further including a wetting agent in an amount sufficient to promote dispersion of the composition in the medium.

25. The composition of claim 24, wherein the wetting agent is a sugar.

26. The composition of claim 25, wherein the wetting agent is dextrose.

27. A dosage for oral administration of the composition of claim 3, containing from about 15 to 25 g of polyethylene glycol.

28. The dosage of the composition of claim 27, containing about 20 g polyethylene glycol.

29. The dosage of claim 27, dissolved or dispersed in from about 6 to 10 fl.oz. of aqueous medium.

30. The dosage of claim 29, wherein the composition further contains a gas-reducing agent derived from fennel seed in an amount sufficient to counteract intestinal gas production.

31. The dosage of claim 30, wherein the composition further comprises a wetting agent in an amount sufficient to disperse the composition in the aqueous medium.

32. A method for improving bowel function in a mammal, comprising orally administering the composition of claim 1 to the mammal, in an amount sufficient to improve bowel motility, stool formation, or both.

33. A method for improving bowel function in a mammal, comprising orally administering polyethylene glycol to the mammal, in an amount sufficient to improve bowel motility, stool formation, or both.

* * * * *